(12) United States Patent
Ushijima et al.

(10) Patent No.: US 10,363,234 B2
(45) Date of Patent: Jul. 30, 2019

(54) ANTIHYPERTENSIVE AGENT

(71) Applicant: WAKUNAGA PHARMACEUTICAL CO., LTD., Osaka-shi (JP)

(72) Inventors: Mitsuyasu Ushijima, Hiroshima (JP); Miyuki Takashima, Hiroshima (JP); Yukihiro Kodera, Hiroshima (JP); Naoaki Morihara, Hiroshima (JP)

(73) Assignee: WAKUNAGA PHARMACEUTICAL CO., LTD., Osaka-shi (JP)

( * ) Notice: Subject to any disclaimer, the term of this patent is extended or adjusted under 35 U.S.C. 154(b) by 0 days.

(21) Appl. No.: 15/580,741

(22) PCT Filed: Jun. 10, 2016

(86) PCT No.: PCT/JP2016/067320
§ 371 (c)(1),
(2) Date: Dec. 8, 2017

(87) PCT Pub. No.: WO2016/199885
PCT Pub. Date: Dec. 15, 2016

(65) Prior Publication Data
US 2018/0147170 A1    May 31, 2018

(30) Foreign Application Priority Data
Jun. 12, 2015 (JP) .................... 2015-119116

(51) Int. Cl.
| | | |
|---|---|---|
| *A61K 31/198* | (2006.01) | |
| *A23L 33/175* | (2016.01) | |
| *A23L 33/105* | (2016.01) | |
| *A61P 9/12* | (2006.01) | |
| *A61K 36/8962* | (2006.01) | |
| *C07C 321/18* | (2006.01) | |

(52) U.S. Cl.
CPC .......... *A61K 31/198* (2013.01); *A23L 33/105* (2016.08); *A23L 33/175* (2016.08); *A61K 36/8962* (2013.01); *A61P 9/12* (2018.01); *C07C 321/18* (2013.01); *A23V 2002/00* (2013.01); *A61K 2236/333* (2013.01); *A61K 2236/53* (2013.01)

(58) Field of Classification Search
None
See application file for complete search history.

(56) References Cited

U.S. PATENT DOCUMENTS

| | | |
|---|---|---|
| 3,892,852 A | 7/1975 | Joullie et al. |
| 6,239,111 B1 | 5/2001 | Moriguchi et al. |
| 2010/0075010 A1* | 3/2010 | Tondeur |

FOREIGN PATENT DOCUMENTS

| | | |
|---|---|---|
| CN | 1895607 A | 1/2007 |
| EP | 3 228 312 A1 | 10/2017 |
| JP | 5-60447 B2 | 9/1993 |
| JP | 2007/45753 A | 2/2007 |
| JP | 4255138 B2 | 4/2009 |
| WO | 2004/077963 A1 | 9/2004 |
| WO | 2016/088892 A1 | 6/2016 |

OTHER PUBLICATIONS

Starkenmann et al., "Nonvolatile S-Alk(en)ylthio-L-cysteine Derivatives in Fresh Onion (*Allium cepa* L. Cultivar)", Journal of Agricultural and Food Chemistry, 2011, vol. 59, pp. 9457-9465.*
Today's Therapy 2012, 2012, pp. 539-580 (with partial English translation of pp. 542,543).
"Garlic Science, First Edition," Wakunaga Pharmaceutical Co., Ltd., 2000, (32 pages), (with partial English translation), pp. 95-122.
Shizutoshi Nakagawa, et al., "Prevention of Liver Damage by Aged Garlic Extract and Its Components in Mice," Phytotherapy Research, vol. 3, No. 2, 1989, (pp. 50-53).
Hiromichi Sumiyoshi, et al., "Chemoprevention of 1,2-Dimethylhydrazine-induced Colon Cancer in Mice by Naturally Occurring Organosulfur Compounds," Cancer Research 50, Aug. 15, 1990, (5 pages).
Reem Shouk, et al., "Mechanisms underlying the antihypertensive effects of garlic bioactives," Nutrition Research, vol. 34, 2014, (pp. 106-115).
K. Ried, et al., "Aged garlic extract reduces blood pressure in hypertensives: a dose-response trial," European Journal of Clinical Nutrition, vol. 67, 2013, (pp. 64-70).
Hidehiko Beppu, et al., "Evaluation of the effects of the ingestion of ajoene, a sulfur containing compound derived from oil-macerated garlic, on metabolic parameters, abdominal circumference, and blood pressure in Japanese metabolic syndrome patients, A pilot study," Journal of Analytical Bio-Science, vol. 33, No. 5, 2010, (pp. 441-450).
Kunio Suetsuna, "Isolation and characterization of angiotensin I-converting enzyme inhibitor dipeptides derived from *Allium sativum* L (garlic)," Journal of Nutritional Biochemistry, vol. 9, Jul. 1998, (pp. 415-419).
International Search Report dated Sep. 13, 2016 in PCT/JP2016/067320 filed Jun. 10, 2016.
Extended European Search Report dated Dec. 21, 2018 for European Patent Application No. 16807590.1.
Marta Corzo-Martinez, et al., "Biological properties of onions and garlic", Trends in Food Science & Technology, vol. 18, pp. 609-625.

* cited by examiner

*Primary Examiner* — Savitha M Rao
*Assistant Examiner* — Gregg Polansky
(74) *Attorney, Agent, or Firm* — Oblon, McClelland, Maier & Neustadt, L.L.P.

(57) ABSTRACT

Provided is an antihypertensive agent that is safe and has a mild effect.
An antihypertensive agent comprising S-1-propenylcysteine or a salt thereof as an active ingredient.

7 Claims, 2 Drawing Sheets

ANTIHYPERTENSIVE AGENT

TECHNICAL FIELD

The present invention relates to an antihypertensive agent.

BACKGROUND ART

Recently, due to changes in people's lifestyles (e.g., an increase in lipid intake in dietary life, an increase in drinking and smoking, and a lack of exercise), so-called life-style related diseases, such as diabetes mellitus, hyperlipemia, hypertension, and gout, which are caused by, for example, accumulation of fat or stress and reduction in liver function, have been rapidly increased, resulting in social problems. As these diseases progress, they result in complications and proceed to diseases ranked among the highest causes of deaths, such as cardiac disease and apoplexy. The latest investigation shows that hypertension is the highest risk factor in the life-style related diseases. Many antihypertensive drugs (e.g., a β blocker, an α blocker, a Ca antagonist or an ACE inhibitor) have been developed.

However, serious side effects have been reported, for example, heart failure and intraventricular block in the case of the β blocker, fainting and dizziness in the case of the α blocker, liver damage in the case of the Ca antagonist, and renal failure in the case of the ACE inhibitor (Non Patent Literature 1). Further, as for these therapeutic drugs, it is difficult to control the blood pressure of potential hypertensive patients, i.e., patients with mild hypertension (e.g., patients with high-normal blood pressure having a maximal blood pressure of 130 to 139/a minimal blood pressure of 85 to 89). Accordingly, there is a need to develop a useful pharmaceutical formulation with less side effects for patients with mild hypertension.

Meanwhile, garlic has been used not only as a food but also for the treatment of various diseases since ancient times. A characteristic component of garlic is γ-glutamyl-S-allyl-cysteine. When garlic is cut, crushed, grated or aged, the component is converted into water-soluble S allylcysteine (hereinafter abbreviated as "SAC") by an enzyme called as γ-glutamyl transpeptidase contained in garlic. Another water soluble compounds which are generated by the above enzymatic reaction include S-methylcysteine and S-1-propenylcysteine, for example, in addition to SAC (Non Patent Literature 2).

It is reported that SAC has many pharmacological effects such as a preventive effect on liver damage (Non Patent Literature 3 and Patent Literature 2) and a preventive effect on colon cancer (Non Patent Literature 4). It is also reported that S-methylcysteine has a preventive effect on liver damage (Patent Literature 2) and an ameliorating effect on brain disease (Patent Literature 1).

However, it has been known that S-1-propenylcysteine has an antihypertensive effect.

CITATION LIST

Patent Literature

Patent Literature 1: JP 4255138 B
Patent Literature 2: JP 05-060447 B

Non Patent Literature

Non Patent Literature 1: Today's Therapy 2012, 539-580, 2012

Non Patent Literature 2: Garlic Science, First Edition, 93-122, 2000
Non Patent Literature 3: Phytother. Res., 3, 50-53, 1989
Non Patent Literature 4: Cancer Res., 50, 5084-5087, 1990

SUMMARY OF THE INVENTION

Technical Problem

The present invention relates to a provision of an antihypertensive agent that has few side effects and has a mild effect.

Solution to Problem

The present inventors have variously studied on the utility of S-1-propenylcysteine or a salt thereof and found that S-1-propenylcysteine or a salt thereof has an excellent antihypertensive effect and is useful as an antihypertensive agent. Then, they have completed the present invention.

That is, the present invention relates to the following 1) to 11):

1) An antihypertensive agent comprising S-1-propenylcysteine or a salt thereof as an active ingredient;
2) The antihypertensive agent according to 1), wherein when the total of a trans-isomer and a cis-isomer is 100%, the rate of the trans-isomer in the S-1-propenylcysteine is from 50 to 100%;
3) The antihypertensive agent according to 1) or 2), wherein the S-1-propenylcysteine or a salt thereof is derived from at least one *Allium* plant selected from the group consisting of garlic, onion, elephant garlic, Chinese chive, and spring onion;
4) The antihypertensive agent according to 3), wherein the S-1-propenylcysteine or a salt thereof is obtained by extracting the *Allium* plant in a 10 to 50% ethanol aqueous solution at 0 to 80° C. for 1 month or more, adsorbing the obtained extract to a cation exchange resin, eluting the adsorbate with 0.1 to 3 N ammonia water, subjecting the eluate to a silica gel column chromatography and/or reverse phase column chromatography, and collecting the resulting eluate;
5) The antihypertensive agent according to any one of 1) to 4), wherein the agent is a medicine;
6) The antihypertensive agent according to any one of 1) to 4), wherein the agent is a food;
7) A food for antihypertension comprising S-1-propenylcysteine or a salt thereof as an active ingredient;
8) A food composition for antihypertension comprising S-1-propenylcysteine or a salt thereof as an active ingredient;
9) Use of S-1-propenylcysteine or a salt thereof for producing an antihypertensive agent;
10) S-1-propenylcysteine or a salt thereof for use in antihypertension;
11) A method for antihypertension comprising administering S-1-propenylcysteine or a salt thereof.

Advantageous Effects of Invention

An excellent antihypertensive effect is observed in S-1-propenylcysteine or a salt thereof as an active ingredient of the antihypertensive agent of the present invention. The antihypertensive function of the antihypertensive agent has a property such that it effectively acts on hypertensive patients, but does not acts on persons with normal blood pressure. The active ingredient has high safety since it is a compound contained in the plant which has been eaten for years. Therefore, according to the present invention, hypertension can be treated and prevented with high safety even in the case of prolonged administration.

DESCRIPTION OF EMBODIMENTS

Figure 1:
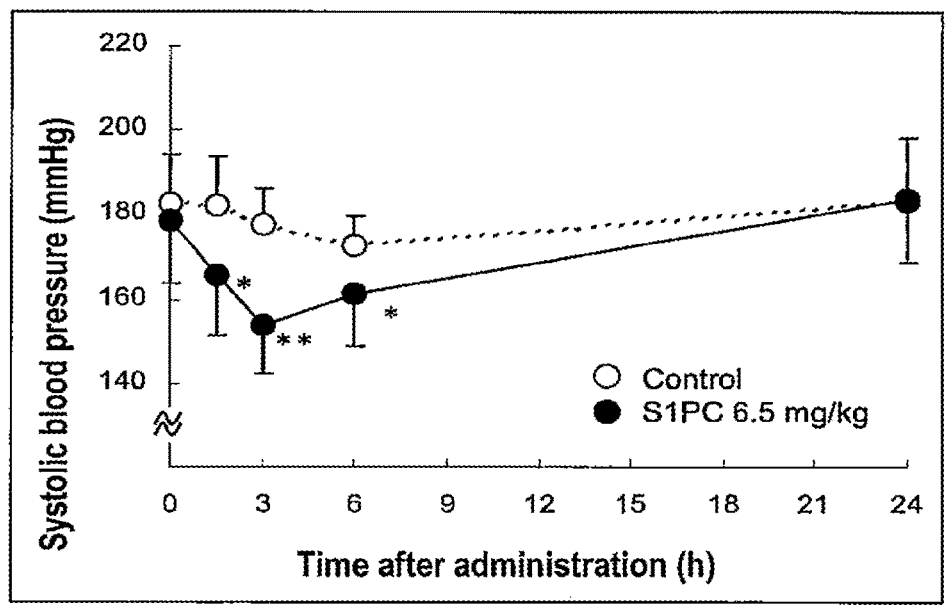
FIG. 1 shows antihypertensive effects of S-1-propenylcysteine (S1PC) in the contraction phase.

In the present invention, S-1-propenylcysteine is a cysteine derivative represented by the following Formula (1).

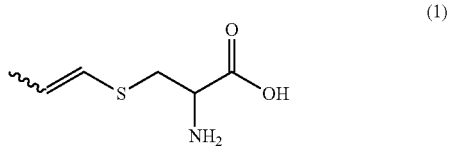

(1)

This compound has a cis or trans configuration as indicated by a wavy line in Formula (1), and the rate of the trans-isomer is preferably high. When the total of the trans-isomer and the cis-isomer is 100%, the rate of the trans-isomer is more preferably from 50 to 100%, still more preferably from 75 to 100%, still more preferably from 80 to 100%, still more preferably from 90 to 100%.

Further, since the compound has an asymmetric carbon derived from cysteine, an optical isomer is present therein and it may be in any of D-form, L-form, and racemic form.

The salt of S-1-propenylcysteine may be either of an acid addition salt or a base addition salt. Examples of the acid addition salt include (a) salts with mineral acids such as hydrochloric acid, sulfuric acid, nitric acid, and phosphoric acid; (b) salts with organic carboxylic acids such as formic acid, acetic acid, citric acid, fumaric acid, gluconic acid, malic acid, succinic acid, tartaric acid, trichloroacetic acid, and trifluoroacetic acid; and (c) salts with sulfonic acids such as methanesulfonic acid, benzenesulfonic acid, p-toluenesulfonic acid, mesitylenesulfonic acid, and naphthalenesulfonic acid. Further, examples of the base addition salt include (a) salts with alkali metals such as sodium and potassium; (b) salts with alkaline earth metals such as calcium and magnesium; (c) ammonium salts; and (d) salts with nitrogen-containing organic bases such as trimethylamine, triethylamine, tributylamine, pyridine, N,N-dimethylaniline, N-methyl piperidine, N-methyl morpholine, diethylamine, dicyclohexylamine, procaine, dibenzylamine, N-benzyl-β-phenethylamine, 1-ephenamine, and N,N'-dibenzyl ethylenediamine.

Further, S-1-propenylcysteine or a salt thereof can exist not only in an unsolvated form but also in the form of a hydrate or solvate. The hydrate or solvate may exist as any crystal form depending on manufacturing conditions. Therefore, S-1-propenylcysteine or a salt thereof in the present invention includes all stereoisomers, hydrates, and solvates, and includes all polymorphic crystal forms or amorphous forms.

S-1-propenylcysteine in the present invention, or its salt can be obtained by an organic synthesis method [1] H Nishimura, A Mizuguchi, J Mizutani, Stereoselective synthesis of S-(trans-prop-1-enyl)-cysteine sulphoxide. Tetrahedron Letter, 1975, 37, 3201-3202; 2] J C Namyslo, C Stanitzek, A palladium-catalyzed synthesis of isoalliin, the main cysteine sulfoxide in Onion (*Allium cepa*). Synthesis, 2006, 20, 3367-3369; 3] S Lee, J N Kim, D H Choung, H K Lee, Facile synthesis of trans-S-1-propenyl-L-cysteine sulfoxide (isoalliin) in onions (*Allium cepa*). Bull. Korean Chem. Soc. 2011, 32(1), 319-320], a biochemical method using enzymes or microorganisms or a method of combination thereof. In addition to these methods, it can be obtained by extracting and purifying from a plant containing the compound, e.g., an *Allium* plant or a processed product thereof.

Therefore, S-1-propenylcysteine or a salt thereof of the present invention to be used may be not only an isolated and purified product, but also a crude product and a fraction in which the content of S-1-propenylcysteine or a salt thereof has been increased by extraction operation from the plant.

Here, examples of the *Allium* plant containing S-1-propenylcysteine or a salt thereof include garlic (*Allium sativum* L.), onion (*Allium cepa* L.), elephant garlic (*Allium ampeloprazum* L.), Chinese chive (*Allium tuberosum*. Rottl. Ex K. Spreng.), and spring onion (*Allium fistulosum* L.). These plants may be used singly, or in combination thereof. Further, the *Allium* plants may be used as they are or may be used after removing their outer skins if necessary and cutting or shredding them. Further, they may be dried by, for example, freeze-drying, or hot air drying, or may be powdered.

When a fraction extracted from the *Allium* plant is used as S-1-propenylcysteine or a salt thereof in the present invention, the fraction can be obtained, for example, by 1) extracting the *Allium* plant in a 10 to 50% ethanol aqueous solution at 0 to 80° C. for 1 month or more; and 2) subjecting the obtained extract to solid liquid separation and collecting ethanol-eluted fractions.

The ethanol aqueous solution used in the step 1) may be a 10 to 50% ethanol aqueous solution, and is preferably an ethanol aqueous solution having an ethanol concentration of 20 to 40%. Further, the treatment temperature may be set to a range of 0 to 80° C., preferably from 10 to 60° C., more preferably from 20 to 40° C. The duration of the extraction treatment under the above conditions is at least one month, preferably from 1 to 20 months, more preferably from 1 to 10 months. Taking into consideration of, for example, sanitation and volatility of ethanol, the present step may be performed in an airtight state, in a hermetically sealed state or in a closed container. It is preferred to use the closed container.

In the step 2), the extract obtained in the step 1) is subjected to solid liquid separation, and then ethanol-eluted fractions are collected. The collected product is concentrated as appropriate so that an extraction fraction containing S-1-propenylcysteine or a salt thereof can be obtained. The extraction fraction may be directly used and may be used after being appropriately dried by spray drying, for example.

Further, S-1-propenylcysteine or a salt thereof can be isolated from the extraction fraction containing S-1-propenylcysteine or a salt thereof by combining a dialysis method using a dialysis membrane with a molecular exclusion size of 3000 to 4000, if necessary, an adsorption/separation method using a cation exchange resin, and a separation/purification method based on normal phase chromatography or reverse phase chromatography.

Here, examples of the adsorption/separation method using a cation exchange resin include a method of adsorbing S-1-propenylcysteine or a salt thereof to a cation exchange resin (e.g., Amberlite (manufactured by Dow Chemical Company), DOWEX (manufactured by Dow Chemical Company), DIAION (manufactured by Mitsubishi Chemical Corporation)) and eluting it with 0.1 to 3 N ammonia water.

Examples of the normal phase chromatography include a method of using a silica gel column and eluting it with a mixture of chloroform/methanol/water.

Examples of the reverse phase chromatography include a method of using an octadecyl silyl column and eluting it with a 0.01 to 3% formic acid aqueous solution.

Preferably, there is a method including the steps of: dialyzing the above ethanol extracted fraction (dialysis membrane; molecular exclusion size: 3000 to 4000); allowing the resultant adsorbed to a cation exchange resin; eluting the adsorbate with 0.5 to 2 N ammonia water; subjecting the eluate to silica gel column chromatography (solvent: a mixture of chloroform/methanol/water) to collect fractions containing a target substance; and further subjecting the fractions to reverse phase column chromatography for fractionation (solvent: a 0.1 to 0.5% formic acid aqueous solution) collect a target substance.

When the total of a trans-isomer and a cis-isomer is 100%, the rate of the trans-isomer in the thus obtained S-1-propenylcysteine is more preferably from 50 to 100%, still more preferably from 60 to 100%, still more preferably from 70 to 100%.

Generally, S-1-propenylcysteine or a salt in the present invention has low toxicity because, for example, the $LD_{50}$ value of a dilute ethanol extract of the garlic as one of the raw materials (extracted component: 14.5%, alcohol number: 1.18) is 50 ml/Kg or more in each of the oral, intra-abdominal, and subcutaneous administration routes (The Journal of Toxicological Sciences, 9,57(1984)), and *Allium* plants such as garlic and onion are regularly used as foods.

As shown in Examples to be described later, S-1-propenylcysteine or a salt thereof has an excellent antihypertensive effect on spontaneous hypertension and an effect of not decreasing normal blood pressure. In other words, S-1-propenylcysteine or a salt thereof can be an antihypertensive agent that works effectively for hypertensive patients, but does not work for individuals with normal blood pressure or individuals with normal blood pressure or less, and can be safely taken.

Hypertension includes secondary hypertension (renal hypertension) whose cause is considered to be an abnormality in the kidney, heart, blood vessel or endocrine system; and essential hypertension whose cause is unknown. The antihypertensive agent in the present invention is effective in both the hypertensions.

The antihypertensive agent of the present invention may be a medicine or food which exerts an antihypertensive effect or may be a material or formulation which is added to them.

Further, the food includes a food which has a concept of use for antihypertension and which is labeled with the concept, if necessary, a functional food, a food for patients, a food for specified health use, and a supplement, for example.

The dosage form of a medicine containing S-1-propenylcysteine or a salt thereof of the present invention is not particularly limited and various dosage forms may be used. Preferred is a dosage form suitable for oral administration. Specific examples of the dosage form of formulation for oral administration include solid formulations such as tablets, capsules, fine granules, pills, and granules; and liquid formulations such as emulsions, solutions, suspensions, and syrups. These medicinal formulations can be prepared by appropriately combining, for example, an excipient, a binder, a disintegrant, a lubricant, a colorant, a corrigent, and a pH-modifier, with S-1-propenylcysteine or a salt thereof of the present invention, if necessary in accordance with an ordinary method.

The form of a food containing S-1-propenylcysteine or a salt thereof of the present invention is not particularly limited. For example, the food may be in the form of various food compositions such as solid foods, semi-liquid foods, gelled foods, tablets, caplets, and capsules, and specifically may be in the form of various foods such as sweets, drinks, seasoning agents, processed sea foods, processed meat foods, bread, and health foods.

The foods can be produced by appropriately blending food materials used to usually produce these foods with S-1-propenylcysteine or a salt thereof of the present invention in accordance with an ordinary method.

The above medicine or food may further contain other substances having an antihypertensive effect, e.g., sulfur-containing amino acids such as γ-glutamyl-S-allylcysteine and SAC, herbal medicines such as *Camellia sasanqua*, *Salvia miltiorrhiza* and *Panax Notoginseng*, amino acids such as glutamic acid and GABA, and peptides such as lactotripeptide and salmon peptide.

The daily intake of the above medicine or food varies depending on factors such as the subject who ingests the medicine or food, the ingestion form, the types of materials and additives to be simultaneously taken, and the intake interval. Usually, the daily intake in terms of S-1-propenylcysteine or a salt thereof is preferably from 0.1 to 2.7 mg/kg, more preferably from 0.3 to 0.9 mg/kg. If desired, this daily intake may be divided into two to four intakes.

EXAMPLES

Production Example 1 Production of Plant-Extracted Fraction Containing S-1-Propenylcysteine (1) Ethanol-Extracted Fraction of Garlic About 1 kg of peeled garlic bulbs and about 1000 mL of 30% ethanol were placed in a container and closed. This container was allowed to stand at room temperature for 1 to 10 months, followed by appropriately stirring. This mixture was separated into a solid and a liquid and the liquid was dried by spray drying to give a yellowish brown powder.

(2) Ethanol-Extracted Fraction of Onion

A peeled onion was cut into two to four pieces. About 5 kg of the cut onions and about 5000 mL of 34% ethanol were placed in a container and closed. This container was allowed to stand at room temperature for 1 to 10 months, followed by appropriately stirring. This mixture was separated into a solid and a liquid and the liquid was concentrated in vacuo.

(3) Ethanol-Extracted Fraction of Chinese Chive

Washed Chinese chives were cut into a length of about 5 to 10 cm. About 5 kg of the cut Chinese chives and about 5000 mL of 34% ethanol were placed in a container and closed. This container was allowed to stand at room temperature for 1 to 10 months, followed by appropriately stirring. This mixture was separated into a solid and a liquid and the liquid was concentrated in vacuo.

Production Example 2 (1) Isolation of S-1-Propenylcysteine from Ethanol-Extracted Fraction of Garlic The ethanol-extracted fraction of garlic obtained in Production Example 1 (1) was put into a dialysis tube having a pore size of 3500 and dialyzed against purified water. The external dialysis solution was passed through a cation exchange resin (Dowex 50Wx8 (H+)) and the resin was washed well with purified water. Amino acids adsorbed to the resin was eluted with 2N ammonia and concentrated in vacuo. The concentrate was placed in a silica gel column, followed by column chromatography using a mixture of chloroform/methanol/water as a solvent. The fractions containing a target substance (S-1-propenylcysteine) were collected and concentrated. The concentrate was dissolved in water and chromatographed on a reverse phase column for fractionation (octadecyl silyl column) with a solvent (0.1% formic acid). A target substance was collected and the solvent was removed by freeze-drying. The resulting freeze-dried substance was compared with the spectrum obtained from the standard substances whose structures are shown below using an NMR (solvent: deuterium oxide) and a mass spectrometer, and confirmed to be a mixture of trans-S-1-propenylcysteine and cis-S-1-propenylcysteine (trans-isomer: cis-isomer=8:2).

trans-S-1-propenylcysteine $^1$H-NMR (500 MHz, in D$_2$O-NaOD, δ): 1.76 (d, 3H, J=7.0 Hz), 2.98 (dd, 1H, J=7.5, 14.5 Hz), 3.14 (dd, 1H, J=4.5, 14.5 Hz), 3.69 (dd, 1H, J=4.5, 7.5 Hz), 5.10-5.14 (m, 1H), 6.02 (d, 1H, J=15.5 Hz);
$^{13}$C-NMR (125 MHz, in D$_2$O-NaOD, δ): 17.61, 33.53, 53.70, 119.92, 132.12, 172.73.
HRMS: observed [M+H]$^+$=162.0583, calculated [M+H]$^+$=162.0581 cis-S-1-propenylcysteine $^1$H-NMR (500 MHz, in D$_2$O, δ): 1.74 (d, 3H, J=7.0 Hz), 3.21 (dd, 1H, J=7.5, 15.0 Hz), 3.31 (dd, 1H, J=4.5, 15.0 Hz), 3.95 (dd, 1H, J=4.5, 7.5 Hz), 5.82-5.86 (m, 1H), 6.01 (d, 1H, J=9.5 Hz);
$^{13}$C-NMR (125 MHz, in D$_2$O-NaOD, δ): 13.89, 33.88, 54.16, 122.58, 127.78, 172.63.
HRMS: observed [M+H]$^+$=162.0580, calculated [M+H]$^+$=162.0581

(2) Measurement of S-1-Propenylcysteine in Ethanol-Extracted Fraction of Garlic 500 mg to 1 g of the ethanol-extracted fraction of garlic obtained in Production Example 1 (1) was transferred into a container, a 20 mM hydrochloric acid solution of S-n-3-butenylcysteine as an internal standard was added thereto and the resultant solution was brought up to 20 mL with 20 mM hydrochloric acid. After stirring the resulting mixture well, a portion thereof was taken out and centrifuged at 1750 G for about 10 minutes. A portion of the obtained supernatant was taken out and subjected to centrifugal filtration (at 15000 rpm for 10 minutes) using a centrifugal filtration unit (Amicon Ultra, cutoff: 3000). 20 μL of the filtrated product was taken out and derivatized with an AccQ-Tag Derivatization Kit (Waters). Separately, a standard compound was dissolved in 20 mM hydrochloric acid and subjected to the same operation as the sample to prepare a standard solution for calibration curve. The sample solution and the standard solution were subjected to chromatography with an Acquity UPLC system (Waters) and the content was determined. As a result, S-1-propenylcysteine was a dry product (3.7±0.3 mg/g).

Test Example 1

Effect of Administering S-1-Propenylcysteine (S1PC) to Spontaneous Hypertensive Rats (SHR)
1. Method
1) Used Animals
One group of eight 8-week-old male SHR/Izm rats purchased from Japan SLC, Inc. (Hamamatsu-shi) was preliminarily bred for two weeks. During preliminary breeding, handling was performed on the rats, and the rats were bred in a constant environment (temperature; 23±1° C., humidity; 50±10%, light-dark cycle; 12 hours (light period; 7 to 19 o'clock)) and freely fed with an artificial diet (CE-2; CLEA Japan, Inc.) and sterilized tap water.
2) Administration Experiment
The administration was performed by forced oral administration using a disposable feeding needle and the fluid volume to be administered was 10 mL per 1 kg of SHR weight. As a sample to be administered, about 15 mg of S-1-propenylcysteine produced in Production Example 2 (a cis- and trans-mixture) was precisely weighed and dissolved in 15 mL of purified water. This solution was used as a stock solution. The solution was appropriately diluted to give a 6.5 mg/kg (SHR weight) of dosage and the diluted solution was orally administered to each of the rats a single time. To each rat of a control group, a solvent (purified water) was orally administered in the same manner as described above.
3) Measurement of Blood Pressure
Before the start of administration (0 hour) and after the administration (1.5, 3, 6, and 24 hours), the systolic blood pressure at the base of each tail was measured without anesthesia using a non-preheating, non-invasive blood pressure monitor (MK-2000ST, Muromachi Kikai Co., Ltd.). Note that the measurement was performed five times per individual, the upper and lower values were eliminated, and an average of the remaining measured values was defined as a systolic blood pressure value of the individual.
2. Results
The results are shown in FIG. 1. In FIG. 1, each white circle represents the control group (purified water) and each black circle represents the group to which 6.5 mg/kg of S-1-propenylcysteine (S1PC) was administered. In FIG. 1, * and ** show that, as the result of comparison of the S-1-propenylcysteine group with the control group at each measurement time, the S-1-propenylcysteine group has a significant difference from the control group (*; p<0.05, **; p<0.01). The t-test was used for examination.
In the case of the single oral dose of S-1-propenylcysteine, a significant antihypertensive effect was shown 1.5 to 6 hours after the administration, as compared with the control group.

Test Example 2

Effect of Administering S-1-Propenylcysteine (S1PC) and S-Allylcysteine (SAC) to Spontaneous Hypertensive Rats (SHR)
1. Method
1) Used Animals
One group of eight 8-week-old male SHR/Izm rats purchased from Japan SLC, Inc. (Hamamatsu-shi) was preliminarily bred for three weeks. During preliminary breeding, handling was performed on the rats, and the rats were bred in a constant environment (temperature; 23±1° C., humidity; 50±10%, light-dark cycle; 12 hours (light period; 7 to 19 o'clock)) and freely fed with an artificial diet (CE-2; CLEA Japan, Inc.) and sterilized tap water.

2) Administration Experiment

The administration was performed by forced oral administration using a disposable feeding needle and the fluid volume to be administered was 10 mL per 1 kg of SHR weight. As a sample to be administered, about 2 mg of S-1-propenylcysteine produced in Production Example 2 (a cis- and trans-mixture) and about 2 mg of S-allylcysteine were precisely weighed and each of them was dissolved in 2 mL of purified water. This solution was used as a stock solution. The solution was appropriately diluted to give a 1 mg/kg (SHR weight) of dosage and the diluted solution was orally administered to each of the rats a single time. To each rat of a control group, a solvent (purified water) was orally administered in the same manner as described above.

3) Measurement of Blood Pressure

Before the start of administration (0 hour) and after the administration (3, 6, and 24 hours), the systolic blood pressure at the base of each tail was measured without anesthesia using a non-preheating, non-invasive blood pressure monitor (MK-2000ST, Muromachi Kikai Co., Ltd.). Note that the measurement was performed five times per individual, the upper and lower values were eliminated, and an average of the remaining measured values was defined as a systolic blood pressure value of the individual.

2. Results

Figure 2:
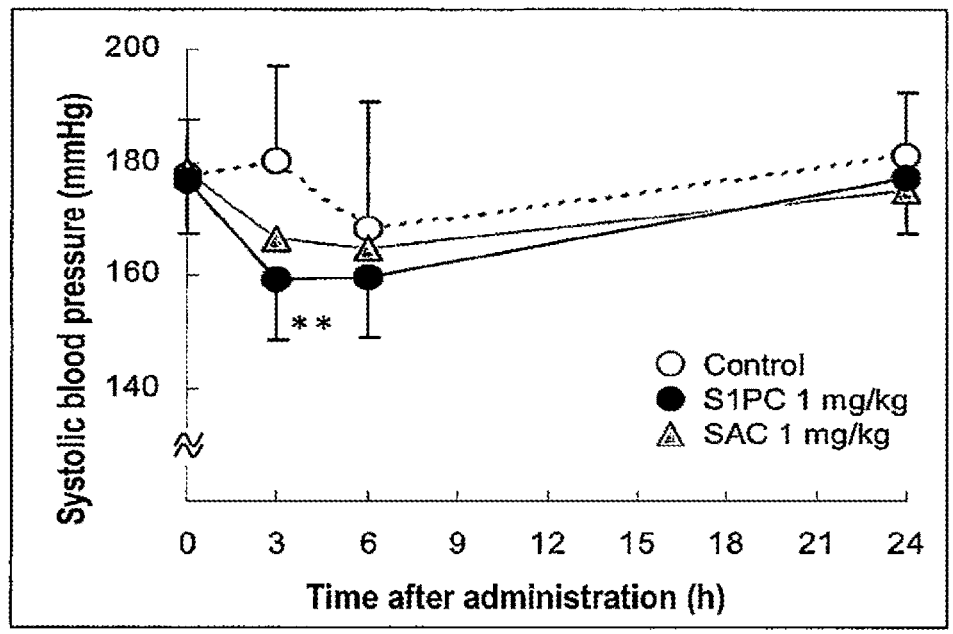
FIG. 2 shows antihypertensive effects of S-1-propenylcysteine (S1PC) and S-allylcysteine (SAC).

The results are shown in FIG. 2. In FIG. 2, each white circle represents the control group (purified water), each black circle represents the group to which 1 mg/kg of S-1-propenylcysteine (S1PC) was administered, and each black triangle represents the group to which 1 mg/kg of S-allylcysteine (SAC) was administered. In FIG. 2,  show that, as the result of comparison of the S1PC group with the control group at each measurement time, the S1PC group has a significant difference from the control group (; $p<0.01$). The Bonferroni test was used for examination.

In the case of the single oral dose of S1PC, a significant antihypertensive effect was shown 3 hours after the administration, as compared with the control group. Meanwhile, in the case of the same single oral dose of SAC, no significant antihypertensive effect was shown.

Test Example 3

Effect of Repeated Oral Administration of S-1-Propenylcysteine (S1PC) on Spontaneous Hypertensive Rats (SHR)

1. Method

1) Used Animals

One group of ten 8-week-old male SHR/Izm rats purchased from Japan SLC, Inc. (Hamamatsu-shi) was preliminarily bred for two weeks. During preliminary breeding, handling was performed on the rats, and the rats were bred in a constant environment (temperature; 23±1° C., humidity; 50±10%, light-dark cycle; 12 hours (light period; 7 to 19 o'clock)) and freely fed with an artificial diet (CE-2; CLEA Japan, Inc.) and sterilized tap water.

2) Administration Experiment

The administration was performed by forced oral administration using a disposable feeding needle and the fluid volume to be administered was 10 mL per 1 kg of SHR weight. As a sample to be administered, about 15 mg of S-1-propenylcysteine produced in Production Example 2 (a cis- and trans-mixture) was precisely weighed and dissolved in 15 mL of purified water. This solution was used as a stock solution. The solution was appropriately diluted to give a 6.5 mg/kg (SHR weight) of dosage and the diluted solution was administered to each of the rats. To each rat of a control group, a solvent (purified water) was orally administered in the same manner as described above. Oral administration was carried out once a day and repeated for 10 weeks.

3) Measurement of Blood Pressure

Before the repeated oral administration (0 hour), and every other week after the administration up to 10 weeks, the systolic blood pressure at the base of each tail was measured without anesthesia using a non-preheating, non-invasive blood pressure monitor (MK-2000ST, Muromachi Kikai Co., Ltd.). Note that the measurement was performed five times per individual, the upper and lower values were eliminated, and an average of the remaining measured values was defined as a systolic blood pressure value of the individual.

2. Results

Figure 3:
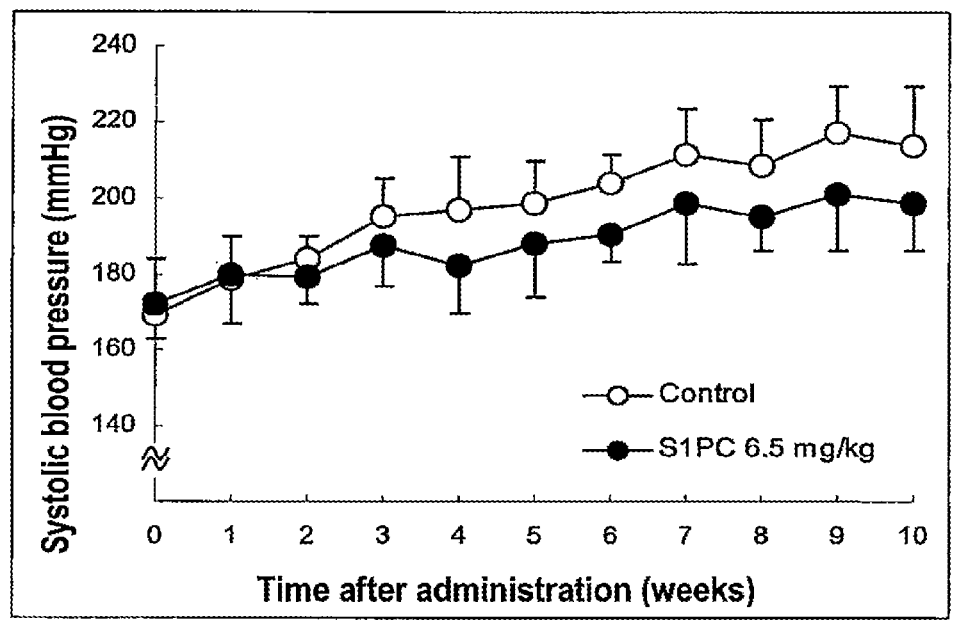
FIG. 3 shows antihypertensive effects of repeated oral administration of S-1-propenylcysteine (S1PC).

The results are shown in FIG. 3. In FIG. 3, each white circle represents the control group (purified water) and each black circle represents the group to which 6.5 mg/kg of S-1-propenylcysteine (S1PC) was administered.

In the case of repeated oral administration of S1PC for 10 weeks, a significant antihypertensive effect was shown, as compared with the control group. The two-way ANOVA was used for examination.

Test Example 4

Effect of Administering S-1-Propenylcysteine (S1PC) to Normotensive Rats (WKY)

1. Method

1) Used Animals

One group of four 8-week-old male WKY/Izm rats purchased from Japan SLC, Inc. (Hamamatsu-shi) was preliminarily bred for two weeks. During preliminary breeding, handling was performed on the rats, and the rats were bred in a constant environment (temperature; 23±1° C., humidity; 50±10%, light-dark cycle; 12 hours (light period; 7 to 19 o'clock)) and freely fed with an artificial diet (CE-2; CLEA Japan, Inc.) and sterilized tap water.

2) Administration Experiment

The administration was performed by forced oral administration using a disposable feeding needle and the fluid volume to be administered was 10 mL per 1 kg of WKY weight. As a sample to be administered, about 15 mg of S-1-propenylcysteine produced in Production Example 2 (a cis- and trans-mixture) was precisely weighed and dissolved in 15 mL of purified water. This solution was used as a stock solution. The solution was appropriately diluted to give a 6.5 mg/kg (WKY weight) of dosage and the diluted solution was orally administered to each of the rats a single time. To each rat of a control group, a solvent (purified water) was orally administered in the same manner as described above.

3) Measurement of Blood Pressure

Before the start of administration (0 hour) and after the administration (3, 6, and 24 hours), the systolic blood pressure at the base of each tail was measured without anesthesia using a non-preheating, non-invasive blood pressure monitor (MK-2000ST, Muromachi Kikai Co., Ltd.). Note that the measurement was performed five times per individual, the upper and lower values were eliminated, and an average of the remaining measured values was defined as a systolic blood pressure value of the individual.

2. Results

Figure 4:
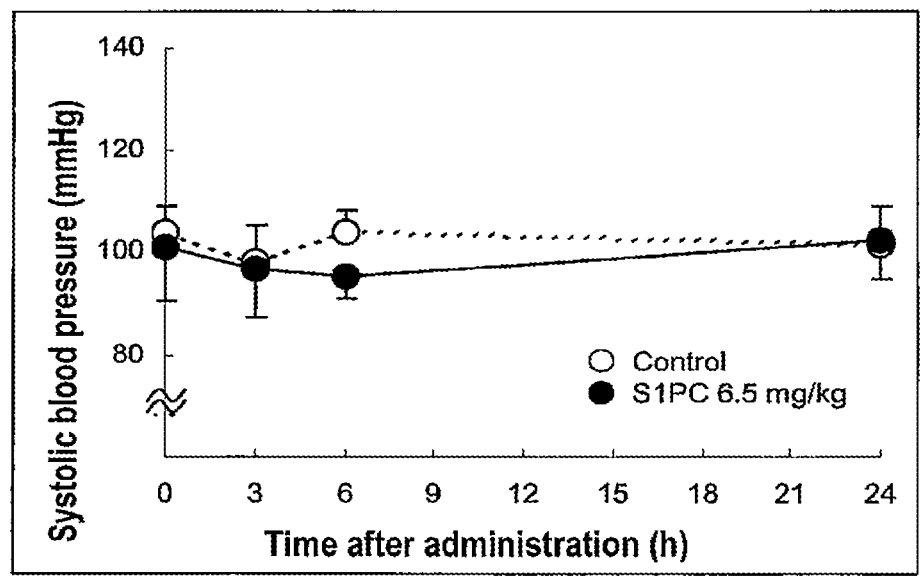
FIG. 4 shows influences of S-1-propenylcysteine (S1PC) on blood pressure of normotensive rats (WKY).

The results are shown in FIG. 4. In FIG. 4, each white circle represents the control group (purified water) and each black circle represents the group to which 6.5 mg/kg of S-1-propenylcysteine (S1PC) was administered.

A single oral administration of S1PC had no significant antihypertensive effect on WKY.

The invention claimed is:

1. A method for antihypertension comprising administering S-1-propenylcysteine or a salt thereof to a subject in need thereof, wherein when a total of a trans-isomer and a cis-isomer of S-1-propenylcysteine or a salt thereof is 100%, the proportion of the trans-isomer in the S-1-propenylcysteine or a salt thereof is from 75 to 100%.

2. The method according to claim 1, wherein the S-1-propenylcysteine or a salt thereof is derived from at least one Allium plant selected from the group consisting of garlic, onion, elephant garlic, Chinese chive, and spring onion.

3. The method according to claim 2, wherein the S-1-propenylcysteine or a salt thereof is obtained by extracting the Allium plant in a 10 to 50% ethanol aqueous solution at 0 to 80° C. for 1 month or more, adsorbing the obtained extract to a cation exchange resin, eluting the adsorbent with 0.1 to 3 N ammonia water, subjecting the eluate to a silica gel column chromatography and/or reverse phase column chromatography, and collecting the resulting eluate.

4. The method according to claim 1, wherein the S-1-propenylcysteine or a salt thereof is present in the form of a medicine.

5. The method according to claim 1, wherein the S-1-propenylcysteine or a salt thereof is present in the form of a food.

6. The method according to claim 1, wherein the proportion of the trans-isomer in the S-1-propenylcysteine or a salt thereof is from 80 to 100%.

7. The method according to claim 1, wherein the proportion of the trans-isomer in the S-1-propenylcysteine or a salt thereof is from 90 to 100%.

* * * * *